(12) United States Patent
Reavill et al.

(10) Patent No.: US 6,380,199 B1
(45) Date of Patent: Apr. 30, 2002

(54) USE OF 5HT$_6$ ANTAGONISTS

(75) Inventors: Charles Alan Reavill; Carol Routledge, both of Hertfordshire (GB)

(73) Assignee: SmithKline Beechan p.l.c., Brentford (GB)

( * ) Notice: Subject to any disclaimer, the term of this patent is extended or adjusted under 35 U.S.C. 154(b) by 0 days.

(21) Appl. No.: 09/763,742

(22) PCT Filed: Aug. 25, 1999

(86) PCT No.: PCT/EP99/06218

§ 371 Date: Apr. 17, 2001

§ 102(e) Date: Apr. 17, 2001

(87) PCT Pub. No.: WO00/12073

PCT Pub. Date: Mar. 9, 2000

(30) Foreign Application Priority Data

Aug. 28, 1998 (GB) .............................. 9818916

(51) Int. Cl.$^7$ ........................ A61K 31/00; A61K 31/495
(52) U.S. Cl. ........................ 514/252.13; 514/252.12; 514/254.02; 514/255.03; 514/602; 514/603; 514/604; 514/605
(58) Field of Search ................................ 514/602, 603, 514/604, 605, 254.02, 252.12, 252.13, 255.03

(56) References Cited

FOREIGN PATENT DOCUMENTS

| WO | WO 98 27081 | 6/1998 |
|---|---|---|
| WO | WO 99 37623 | 7/1999 |

OTHER PUBLICATIONS

Rogers D C_(A) J_(A): "Cognitive enhancement effects of the selective 5–HT6 antagonist #SB#–#271046#." British Journal of Pharmacology, 1999, vol. 127, no. proc. suppl. Jun. 1999, p. 22p XP000965803 the whole document.

Primary Examiner—Frederick Krass
(74) Attorney, Agent, or Firm—Soma G. Simon; Charles M. Kinzig; William T. King

(57) ABSTRACT

A method of treating ADHD comprising administering a 5-HT$_6$ receptor antagonist according to formula (A) hereinbelow:

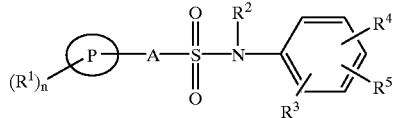

wherein:

P is phenyl, naphthyl, a bicyclic heterocyclic ring or is a 5 to 7-membered heterocyclic ring each containing 1 to 4 heteroatoms selected from oxygen, nitrogen or sulphur;

A is a single bond, a $C_{1-6}$alkylene or a $C_{1-6}$alkenylene group;

$R^1$ is halogen, $C_{1-6}$alkyl optionally substituted by one or more halogen atoms, $C_{3-6}$cycloalkyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, nitro, amino, $C_{1-6}$alkylamino or di$C_{1-6}$alkylamino, cyano or $R^1$ is phenyl, naphthyl, a bicyclic heterocyclic ring or is a 5 to 7-membered heterocyclic ring each containing 1 to 4 heteroatoms selected from oxygen, nitrogen or sulphur;

n is 0, 1, 2, 3, 4, 5 or 6, $R^2$ is hydrogen, $C_{1-6}$ alkyl or aryl $C_{1-6}$ alkyl;

$R^3$ is a group $R^5$ or together with $R^5$ forms a group $(CH_2)_2O$ or $(CH_2)_3O$ or $R^3$ is linked to $R^2$ to form a group $(CH_2)_2$ or $(CH_2)_3$;

$R^4$ is —X(CH$_2$)p—R$^6$ where X is a single bond, CH$_2$, O, NH or N—C$_{1-6}$ alkyl and p is 0 to 6 and R$^6$ is an optionally substituted 5- to 7-membered heterocyclic ring containing 1 to 3 heteroatoms selected from nitrogen, sulphur or oxygen, or $R^6$ is NR$^7$R$^8$ where R$^7$ and R$^8$ are independently hydrogen, $C_{1-6}$ alkyl or aryl$C_{1-6}$alkyl; and $R^5$ is hydrogen, halogen, $C_{1-6}$alkyl, $C_{3-6}$cycloalkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, nitro, trifluoromethyl, cyano or aryl.

4 Claims, No Drawings

USE OF 5HT$_6$ ANTAGONISTS

This application is a 371 of PCT/EP99/06218, filed Aug. 25, 1997.

The present invention relates to the use of compounds known in the art as 5-HT$_6$ receptor antagonists in the treatment of hyperactivity disorders. More particularly the invention relates to the use of such compounds in the treatment of Attention Deficit Hyperactivity Disorder (ADHD).

Attention Deficit Hyperactivity Disorder, which is also referred to in the literature as Attention Deficit Disorder/Hyperactivity Syndrome (ADD/HS), is a condition (or group of conditions) characterised by impulsiveness, distractibility, inappropriate behaviour in social situations and hyperactivity. ADD/HS is reported to have a prevalence of 3–5% (using DSM-IV criteria) in children (Diagnostic and Statistical Manual of Mental Disorders; 4th edition; American Psychiatric Association; 1994). It is believed that some 30–60% of such cases persist into adulthood (Zametkin A. J. and Borcherding B. G., Ann. Rev. Med. 1989, 40:447–51). This disorder can impair social function, learning and/or development and is therefore now recognised as a serious problem. It is further recognised that many children with ADHD go on to develop other comorbid conditions or social problems in adulthood.

In clinical terms ADHD is diagnosed if any one of the three main clinical features viz. inattention, over-activity and impulsiveness, persists in two or more situations, e.g. in both a home and school environment (American Psychiatric Association. Diagnostic and Statistical Manual of Mental Disorders, Fourth Edition (DSM-IV) Washington, D.C.: American Psychiatric Association, 1994).

A particularly severe form of ADHD is termed Hyperkinetic Disorder. In Britain, this diagnosis is made only if all three of the main clinical features (inattention, over-activity and impulsiveness) have been present from an early age, persist in more than one situation (e.g. home and school) and impair function (The ICD-10 Classification of Mental and Behavioural Disorders: Diagnostic Criteria for Research. Geneva: World Health Organisation, 1993: 155–7). Reports indicate that 1 in 200 children suffer from hyperkinetic disorder (Taylor E., et al, The Epidemiology of Childhood Hyperactivity, Oxford University Press 1991: 93–113).

There are currently only a few therapeutic agents which are recognised as having efficacy in the treatment of childhood ADHD; at present the drugs of choice are dextroamphetamine, pemoline and in particular methylphenidate (Ritalin, ™). Antidepressants and antipsychotic medications such as risperidone may also be effective in some cases but these are not standard treatments. Although methylphenidate is probably the most widely used drug in the treatment of ADHD it suffers from a number of disadvantages: it is a controlled drug: is extensively metabolised and may cause confusion and hallucinations. Moreover, methylphenidate does not treat one of the three main clinical features of ADHD, namely inattentiveness, and in addition does not normalise ADHD children. There is therefore a need for a new treatment for ADHD and related disorders which demonstrate both an improved pharmacological profile and which do not have the associated disadvantages of currently known therapeutic agents.

The etiology of ADHD is still not well understood. However, there is evidence to suggest that ADHD is associated with abnormalities in the caudate (Ernst et al, Journal of Neuroscience, 1998, 18(15), 5901–5907.). It has now been found that certain compounds, known in the art as 5-HT$_6$ receptor antagonists, selectively increases activity of the nigrostriatal dopamine pathway and could therefore, specifically alleviate these abnormalities. The compounds of the present invention have additional effects on the central nervous system, namely, an increase in cognitive function. Consequently, such compounds have utility in the treatment of ADHD and related disorders.

The present invention therefore provides, in a first aspect, the use of a compound having 5-HT$_6$ receptor antagonist activity in the manufacture of a medicament for use in the treatment of ADHD.

A 5-HT$_6$ antagonist for use in this invention must be selective for 5-HT$_6$ receptors. Where used herein, this is intended to mean that the 5-HT$_6$ antagonist must have a greater than 10-fold selectivity for this receptor over other binding sites within the CNS, in particular, other 5-HT receptor sub-types and dopaminergic receptors. The most preferred compounds of this invention demonstrate greater than 100-fold selectivity for 5-HT$_6$ receptors. The selectivity of the compounds of this invention for 5-HT$_6$ receptors can be determined using binding assays methods which are well known to those skilled in the art.

Preferred compounds of this invention include those disclosed in patent applications WO 98/27081 (SmithKline Beecham p.l.c.) and WO 99/02502 (SmithKline Beecham p.l.c.). Compounds of this invention therefore include compounds of formula (A) and compounds of formula (B), which can be prepared according to methods described in WO 98/27081 and WO 99/02502 respectively.

Compounds of Formula (A)

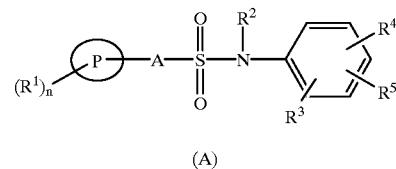

(A)

wherein:

P is phenyl, naphthyl, a bicyclic heterocyclic ring or is a 5 to 7-membered heterocyclic ring each containing 1 to 4 heteroatoms selected from oxygen, nitrogen or sulphur;

A is a single bond, a $C_{1-6}$alkylene or a $C_{1-6}$alkenylene group;

$R^1$ is halogen, $C_{1-6}$alkyl optionally substituted by one or more halogen atoms, $C_{3-6}$cycloalkyl, $C_{1-6}$alkyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, nitro, amino, $C_{1-6}$alkylamino or di$C_{1-6}$alkylamino, cyano or $R^1$ is phenyl, naphthyl, a bicyclic heterocyclic ring or is a 5 to 7-membered heterocyclic ring each containing 1 to 4 heteroatoms selected from oxygen, nitrogen or sulphur;

n is 0, 1, 2, 3, 4, 5 or 6, $R^2$ is hydrogen, $C_{1-6}$ alkyl or aryl$C_{1-6}$ alkyl;

$R^3$ is a group $R^5$ or together with $R^5$ forms a group $(CH_2)_2O$ or $(CH_2)_3O$ or $R^3$ is linked to $R^2$ to form a group $(CH_2)_2$ or $(CH_2)_3$;

$R^4$ is —$X(CH_2)p$—$R^6$ where X is a single bond, $CH_2$, O, NH or N—$C_{1-6}$ alkyl and p is 0 to 6 and $R^6$ is an optionally substituted 5- to 7-membered heterocyclic ring containing 1 to 3 heteroatoms selected from nitrogen, sulphur or oxygen, or $R^6$ is $NR^7R^8$ where $R^7$ and $R^8$ are independently hydrogen, $C_{16}$ alkyl or aryl $C_{16}$ alkyl; and $R^5$ is hydrogen, halogen, $C_{1-6}$alkyl, $C_{3-6}$cycloalkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, nitro, trifluoromethyl, cyano or aryl.

Compounds of Formula (B)

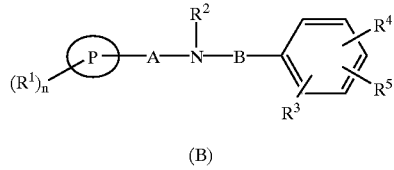

(B)

wherein:

P is phenyl, naphthyl, anthracenyl, a bicyclic heterocyclic ring, a tricyclic heteroaromatic ring or is a 5 to 7-membered heterocyclic ring each containing 1 to 4 heteroatoms selected from oxygen, nitrogen or sulphur;

A is a single bond, a $C_{1-6}$alkylene or a $C_{1-6}$alkenylene group;

B is $SO_2$;

$R^1$ is halogen, $C_{1-6}$alkyl optionally substituted by one or more fluorine atoms, $C_{3-6}$cycloalkyl, $C_{2-6}$alkenyl, $C_{2-6}$alkynyl, $C_{1-6}$alkanoyl $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, nitro, cyano, $NR^{10}R^{11}$ where $R^{10}$ and $R^{11}$ are independently hydrogen, $C_{1-6}$alkyl or optionally substituted phenyl, $SR^{11}$ where $R^{11}$ is as defined above or $R^1$ is optionally substituted phenyl, naphthyl, a bicyclic heterocyclic ring or is a 5 to 7-membered heterocyclic ring each containing 1 to 4 heteroatoms selected from oxygen, nitrogen or sulphur, or $R^1$ together with a second $R^1$ substituent forms a group $-O-CH_2-O-$, $OCH_2CH_2O-$, $-CH_2CH_2CH_2-$ or $-CH_2CH_2CH_2CH_2-$, n is 0, 1, 2, 3, 4, 5 or 6;

$R^2$ is hydrogen, $C_{1-6}$alkyl, aryl$C_{1-6}$ alkyl or together with group P form a 5 to 8 membered ring optionally substituted with one or more $C_{1-6}$alkyl groups;

$R^3$ is hydrogen, halogen, $C_{1-6}$alkyl, $C_{3-6}$cycloalkyl, $C_{1-6}$alkanoyl, $C_{1-6}$alkoxy optionally substituted with one or more fluorine atoms, hydroxy, hydroxy$C_{1-6}$alkyl, hydroxy$C_{1-6}$alkoxy, $C_{1-6}$alkoxy$C_{1-6}$alkoxy, nitro, trifluoromethyl, cyano or aryl or together with the group $R^5$ forms a group $(CH_2)_2O$ or $(CH_2)_3O$ optionally substituted with 1 or more $C_{1-6}$alkyl groups;

$R^4$ is $-X(CH_2)p-R^6$ where X is a single bond, $CH_2$, O, NH or N-alkyl and p is 0 to 6 and $R^6$ is an optionally substituted 4- to 7-membered heterocyclic ring containing 1 to 3 heteroatoms selected from nitrogen, sulphur or oxygen, or $R^6$ is $NR^7R^8$ where $R^7$ and $R^8$ are independently hydrogen, $C_{1-6}$alkyl or aryl$C_{1-6}$ alkyl; and $R^5$ is a group $R^3$ or together with $R^3$ forms a group $(CH_2)_2O$ or $(CH_2)_3O$ optionally substituted with 1 or more $C_{1-6}$alkyl groups.

Other compounds for use in this invention include those generically and specifically disclosed in patent application WO 97/27058 (SmithKline Beecham) and European patent applications EP 0815861 (Hoffman-la-Roche) and EP 0930302 (Hoffman-la-Roche).

Particularly preferred compounds of this invention include 5-Chloro-3-methylbenzo[b]thiophene-2-sulfonic acid (4-methoxy-3-piperazin-1-ylphenyl) amide (Example 83 in WO 98/27081), that is to say, the compound of formula (I)

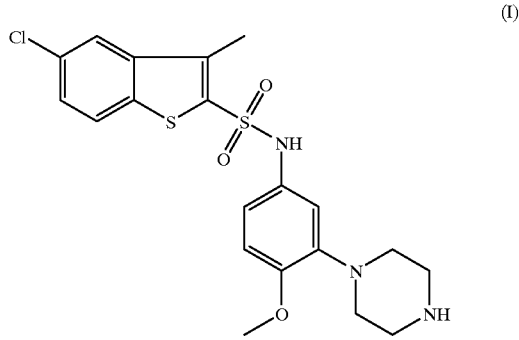

and N-(2,5-Dibromo-3-fluorophenyl)-4-methoxy-3-piperazin-1-ylbenzenesulfonamide (Example 140 in WO 99/02502) that is to say, the compound of formula (II)

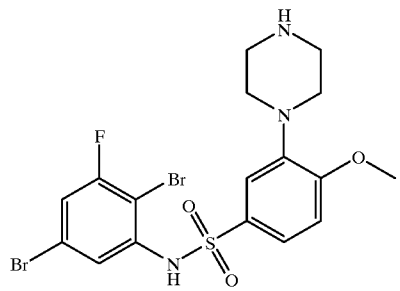

Compounds exhibiting 5-$HT_6$ receptor antagonist activity may form acid addition salts with acids, such as conventional pharmaceutically acceptable acids, for example maleic, hydrochloric, hydrobromic, phosphoric, acetic, fumaric, salicylic, sulphate, citric, lactic, mandelic, tartaric and methanesulphonic. Salts of 5-HT6 receptor antagonists therefore form an aspect of the invention. Suitably, a compound of formula (I) and (II) are used as the hydrochloride salt.

Certain compounds exhibiting 5-$HT_6$ antagonist activity are capable of existing in stereoisomeric forms. It will be understood that the invention encompasses all geometric and optical isomers of these compounds and the mixtures thereof including racemates. Tautomers also form an aspect of the invention.

The present invention further provides a method of treatment of ADHD and other related disorders which comprises administering to a host in need thereof an effective amount of a 5-$HT_6$ receptor antagonist or a pharmaceutically acceptable salt thereof.

When used in therapy, the 5-$HT_6$ receptor antagonists are usually formulated in a standard pharmaceutical composition. Such compositions can be prepared using standard procedures.

A pharmaceutical composition of the invention which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

What is claimed is:

1. A method of treating ADHD comprising administering a 5-HT$_6$ receptor antagonist of formula (A) hereinbelow to a subject having ADHD:

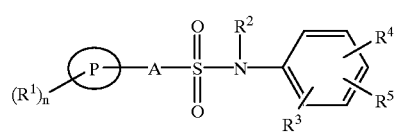

(A)

wherein:
P is phenyl, naphthyl, a bicyclic heterocyclic ring or is a 5 to 7-membered heterocyclic ring each containing 1 to 4 heteroatoms selected from oxygen, nitrogen or sulphur;

A is a single bond, a $C_{1-6}$alkylene or a $C_{1-6}$alkenylene group;

$R^1$ is halogen, $C_{1-6}$alkyl optionally substituted by one or more halogen atoms, $C_{3-6}$cycloalkyl, $C_{1-6}$alkoxy, $OCF_3$, hydroxy, $C_{1-6}$alkyl substituted with hydroxy, $C_{1-6}$alkoxy substituted with hydroxy, $C_{1-6}$alkyloxy substituted with $C_{1-6}$alkoxy, $C_{1-6}$alkanoyl, nitro, amino, $C_{1-6}$alkylamino or di$C_{1-6}$alkylamino, cyano or $R^1$ is phenyl, naphthyl, a bicyclic heterocyclic ring or is a 5 to 7-membered heterocyclic ring each containing 1 to 4 heteroatoms selected from oxygen, nitrogen or sulphur;

n is 0, 1, 2, 3, 4, 5 or 6, $R^2$ is hydrogen, $C_{1-6}$ alkyl or aryl $C_{1-6}$ alkyl;

$R^3$ is a group $R^5$ or together with $R^5$ forms a group $(CH_2)_2O$ or $(CH_2)_3O$ or $R^3$ is linked to $R^2$ to form a group $(CH_2)_2$ or $(CH_2)_3$;

$R^4$ is —X(CH$_2$)p—$R^6$ where X is a single bond, CH$_2$, O, NH or N—C$_{1-6}$ alkyl and p is 0 to 6 and $R^6$ is an optionally substituted 5- to 7-membered heterocyclic ring containing 1 to 3 heteroatoms selected from nitrogen, sulphur or oxygen, or $R^6$ is NR$^7$R$^8$ where $R^7$ and $R^8$ are independently hydrogen, $C_{1-6}$ alkyl or aryl$C_{1-6}$alkyl; and $R^5$ is hydrogen, halogen, $C_{1-6}$alkyl, $C_{3-6}$cycloalkyl, $C_{1-6}$alkoxy, hydroxy, $C_{1-6}$alkyl substituted with hydroxy, $C_{1-6}$alkoxy substituted with hydroxy, $C_{1-6}$alkyloxy substituted with $C_{1-6}$alkoxy, $C_{1-6}$alkanoyl, nitro, trifluoromethyl, cyano or aryl or a pharmaceutically acceptable salt thereof.

2. A method according to claim 1 wherein the 5-HT$_6$ receptor antagonist is the compound of formula (I) (5-Chloro-3-methylbenzo[b]thiophene-2-sulfonic acid (4-methoxy-3-piperazin-1-ylphenyl)amide) or a pharmaceutically acceptable salt thereof

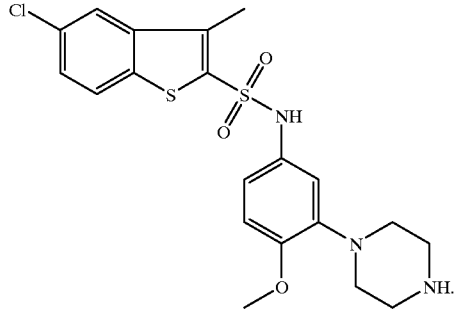

(I)

3. A method of treating ADHD comprising administering a 5-HT$_6$ receptor antagonist of formula (B) or a pharmaceutically acceptable salt thereof to a subject having ADHD

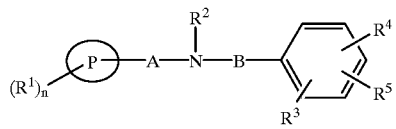

(B)

wherein:
P is phenyl, naphthyl, anthracenyl, a bicyclic heterocyclic ring, a tricyclic heteroaromatic ring or is a 5 to 7-membered heterocyclic ring each containing 1 to 4 heteroatoms selected from oxygen, nitrogen or sulphur;

A is a single bond, a $C_{1-6}$alkylene or a $C_{1-6}$alkenylene group;

B is SO$_2$;

$R^1$ is halogen, $C_{1-6}$alkyl optionally substituted by one or more fluorine atoms, $C_{3-6}$cycloalkyl, $C_{2-6}$alkenyl, $C_{2-6}$alkynyl, $C_{1-6}$alkanoyl, $C_{1-6}$alkoxy, $OCF_3$, hydroxy, $C_{1-6}$alkyl substituted with hydroxy, $C_{1-6}$alkoxy substituted with hydroxy, $C_{1-6}$alkyloxy substituted with $C_{1-6}$alkoxy, nitro, cyano, $NR^{10}R^{11}$ where $R^{10}$ and $R^{11}$ are independently hydrogen, $C_{1-6}$alkyl or optionally substituted phenyl, $SR^{11}$ where $R^{11}$ is as defined above or $R^1$ is optionally substituted phenyl, naphthyl, a bicyclic heterocyclic ring or is a 5 to 7-membered heterocyclic ring each containing 1 to 4 heteroatoms selected from oxygen, nitrogen or sulphur, or $R^1$ together with a second $R^1$ substituent forms a group —O—CH$_2$—O—, OCH$_2$CH$_2$O—, —CH$_2$CH$_2$CH$_2$— or —CH$_2$CH$_2$CH$_2$CH$_2$—, n is 0, 1, 2, 3, 4, 5 or 6;

$R^2$ is hydrogen, $C_{1-6}$alkyl, aryl$C_{1-6}$alkyl or together with group P forms a 5 to 8 membered ring optionally substituted with one or more $C_{1-6}$alkyl groups;

$R^3$ is hydrogen, halogen, $C_{1-6}$alkyl, $C_{3-6}$cycloalkyl, $C_{1-6}$alkanoyl, $C_{1-6}$alkoxy optionally substituted with one or more fluorine atoms, hydroxy, $C_{1-6}$alkyl substituted with hydroxy, $C_{1-6}$alkoxy substituted with hydroxy, $C_{1-6}$alkyloxy substituted with $C_{1-6}$alkoxy, nitro, trifluoromethyl, cyano or aryl or together with the group $R^5$ forms a group (CH$_2$)$_2$O or (CH$_2$)$_3$O optionally substituted with 1 or more $C_{1-6}$alkyl groups;

$R^4$ is —X(CH$_2$)p—$R^6$ where X is a single bond, CH$_2$, O, NH or N-alkyl and p is 0 to 6 and $R^6$ is an optionally substituted 4- to 7-membered heterocyclic ring containing 1 to 3 heteroatoms selected from nitrogen, sulphur or oxygen, or $R^6$ is $NR^7R^8$ where $R^7$ and $R^8$ are independently hydrogen, $C_{1-6}$ alkyl or aryl$C_{1-6}$ alkyl; and $R^5$ is a group $R^3$ or together with $R^3$ forms a group (CH$_2$)$_2$O or (CH$_2$)$_3$O optionally substituted with 1 or more $C_{1-6}$alkyl groups.

4. A method according to claim 3 wherein the 5-HT$_6$ receptor antagonist is the compound of formula (II) (N-(2,5-Dibromo-3-fluorophenyl)-4-methoxy-3-piperazin-1-ylbenzenesulfonamide) or a pharmaceutically acceptable salt thereof (II)

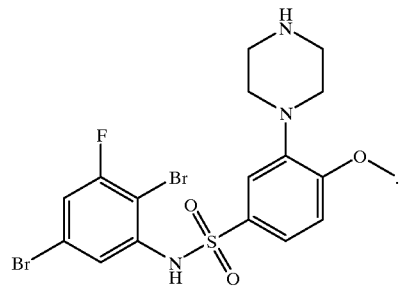

* * * * *